United States Patent
Ishii et al.

(10) Patent No.: US 6,403,521 B1
(45) Date of Patent: Jun. 11, 2002

(54) CATALYST COMPRISING NITROGEN-CONTAINING HETEROCYCLIC COMPOUND, AND PROCESS FOR PRODUCING ORGANIC COMPOUND USING THE CATALYST

(75) Inventors: Yasutaka Ishii, Takatsuki; Tatsuya Nakano, Himeji, both of (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/653,953

(22) Filed: Sep. 1, 2000

(30) Foreign Application Priority Data

Sep. 1, 1999 (JP) ............................. 11-248084

(51) Int. Cl.⁷ ..................... B01J 31/00; C07D 311/80; C07D 249/16; C07D 251/00
(52) U.S. Cl. ..................... 502/150; 502/152; 502/155; 502/162; 502/204; 502/213; 549/390; 548/257; 548/259; 544/180; 544/215
(58) Field of Search ................ 502/150, 152, 502/155, 162, 204, 213; 549/390; 548/259; 544/180, 215

(56) References Cited

U.S. PATENT DOCUMENTS 6,121,471 A  *  9/2000  Scott ......................... 554/69
6,284,895 B1 *  9/2001  Thanki et al. .............. 548/260
6,297,377 B1 * 10/2001  Gupta et al. ............... 544/215

* cited by examiner

*Primary Examiner*—Deborah C. Lambkin
(74) *Attorney, Agent, or Firm*—Birch, Stewart, Kolasch & Birch, LLP

(57) ABSTRACT

A catalyst is for use in a reaction using an oxygen-atom-containing reactant and includes a nitrogen-containing heterocyclic compound of the following formula (1):

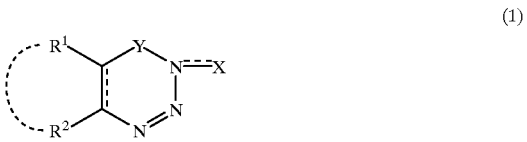

(1)

wherein each of $R^1$ and $R^2$ is, identical to or different from each other, a hydrogen atom, a halogen atom, an alkyl group, a haloalkyl group, an aryl group, a cycloalkyl group, a hydroxyl group, an alkoxy group, a carboxyl group, an alkoxycarbonyl group, or an acyl group, and $R^1$ and $R^2$ may be combined to form a double bond or to form an aromatic or non-aromatic ring with the adjacent two carbon atoms, where one or two of heterocyclic ring containing three nitrogen atoms indicated in the formula may be further formed on the $R^1$ or $R^2$, or on the double bond or aromatic or non-aromatic ring formed by $R^1$ and $R^2$; X is an oxygen atom or a hydroxyl group; and Y is a single bond, a methylene group, or a carbonyl group. This catalyst can introduce an oxygen-atom-containing group into an organic substrate under mild conditions.

5 Claims, No Drawings

CATALYST COMPRISING NITROGEN-CONTAINING HETEROCYCLIC COMPOUND, AND PROCESS FOR PRODUCING ORGANIC COMPOUND USING THE CATALYST

BACKGROUND OF THE INVENTION

1. Field of the Invention

The present invention relates to a catalyst which is useful for oxidation, nitration, carboxylation, and other reactions for introducing a group containing at least an oxygen atom into an organic substrate, and to a process for producing an organic compound using the catalyst.

2. Description of the Related Art

Oxidation reaction is one of the most basic reactions in organic chemical industries, and a variety of oxidation processes are known. For example, a process is known which includes the step of oxidizing a methyl group, or a methylene group or methine group corresponding to the benzyl position on an aromatic ring, an alcohol or a carbonyl compound with nitric acid to yield a corresponding carboxylic acid. However, this oxidation process using nitric acid invites by-production of nitrogen oxides and therefore requires expensive treating facilities of exhaust gas. In another known oxidation process, a substrate is oxidized with molecular oxygen in the presence of a metallic compound catalyst such as a cobalt catalyst. However, this process can be applied only within a narrow range and requires extreme conditions such as high temperatures and high pressures upon oxidation of some substrates.

On the other hand, a process using a mixed acid (a mixture of nitric acid and sulfuric acid) is in wide use as a process for the nitration of hydrocarbons. However, this process requires the use of highly concentrated strong acids in large amounts, and in addition, invites by-production of nitrogen oxides in large amounts as in the nitric acid oxidation process. The process in question therefore requires treating facilities for these substances.

As for carboxylation, few processes are known to introduce a carboxyl group directly into a hydrocarbon under mild conditions.

As is described, an oxygen-atom-containing group such as a hydroxyl group, a nitro group, or a carboxyl group cannot be generally significantly introduced into an organic substrate under mild conditions.

SUMMARY OF THE INVENTION

Accordingly, an object of the invention is to provide a catalyst which can introduce an oxygen-atom-containing group into an organic substrate under mild conditions, and to provide a process for producing an organic compound using the catalyst.

Another object of the invention is to provide a highly versatile catalyst which can be applied to a wide variety of reactions using oxygen-atom-containing reactants, and to provide a process for producing an organic compound using the catalyst.

A further object of the invention is to provide a catalyst which requires no exhaust gas treating facilities and can introduce an oxygen-atom-containing group into an organic substrate even by the use of the catalyst in a small amount, and to provide a process for producing an organic compound using the catalyst.

After intensive investigations to achieve the above objects, the present inventors found that when an organic substrate is allowed to react with an oxygen-atom-containing reactant such as oxygen in the presence of a nitrogen-containing heterocyclic compound having a specific structure, an oxygen-atom-containing group such as a hydroxyl group can be introduced into the organic substrate under mild conditions. The present invention has been accomplished based on these findings.

Specifically, the invention provides, in an aspect, a catalyst for a reaction using an oxygen-atom-containing reactant. This catalyst includes a nitrogen-containing heterocyclic compound shown by the following formula (1):

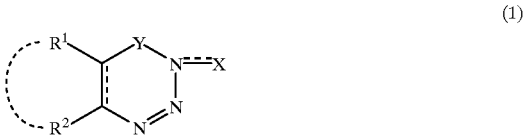

wherein each of $R^1$ and $R^2$ is, identical to or different from each other, a hydrogen atom, a halogen atom, an alkyl group, a haloalkyl group, an aryl group, a cycloalkyl group, a hydroxyl group, an alkoxy group, a carboxyl group, an alkoxycarbonyl group, or an acyl group, and $R^1$ and $R^2$ may be combined to form a double bond or to form an aromatic or non-aromatic ring with the adjacent two carbon atoms, where one or two of heterocyclic ring containing three nitrogen atoms indicated in the formula may be further formed on the $R^1$ or $R^2$, or on the double bond or aromatic or non-aromatic ring formed by $R^1$ and $R^2$; X is an oxygen atom or a hydroxyl group; and Y is a single bond, a methylene group, or a carbonyl group.

In another aspect, the invention provides a process for producing an organic compound. This process includes the step of allowing an organic substrate to react with an oxygen-atom-containing reactant in the presence of the aforementioned catalyst to yield a product, to the product a group containing at least an oxygen atom is introduced.

DESCRIPTION OF THE PREFERRED EMBODIMENTS

[Nitrogen-containing Heterocyclic Compound]

Of the substituents $R^1$ and $R^2$ in the nitrogen-containing heterocyclic compound of the formula (1), the halogen atom includes, for example, iodine, bromine, chlorine, and fluorine atoms. Illustrative alkyl groups are methyl, ethyl, propyl, isopropyl, butyl, isobutyl, s-butyl, t-butyl, hexyl, decyl, and other straight- or branched-chain alkyl groups each having about 1 to 10 carbon atoms. Preferred alkyl groups are alkyl groups each having about 1 to 6 carbon atoms, of which lower alkyl groups each having about 1 to 4 carbon atoms are particularly preferred. The haloalkyl group includes, for example, trifluoromethyl group, and other haloalkyl groups each having about 1 to 4 carbon atoms.

The aryl group includes phenyl and naphthyl groups, for example. Illustrative cycloalkyl groups include cyclopentyl and cyclohexyl groups. Illustrative alkoxy groups are methoxy, ethoxy, isopropoxy, butoxy, t-butoxy, hexyloxy, and other alkoxy groups each having about 1 to 10 carbon atoms, and preferably having about 1 to 6 carbon atoms. Among them, lower alkoxy groups each having about 1 to 4 carbon atoms are especially preferred.

Illustrative alkoxycarbonyl groups include methoxycarbonyl, ethoxycarbonyl, isopropoxycarbonyl, butoxycarbonyl, t-butoxycarbonyl, hexyloxycarbonyl, and other alkoxycarbonyl groups each having about 1 to 10 carbon atoms in the alkoxy moiety. Preferred alkoxycarbonyl groups are alkoxycarbonyl groups each having about 1 to 6 carbon atoms in the alkoxy moiety, of which lower alkoxycarbonyl groups each having about 1 to 4 carbon atoms in the alkoxy moiety are particularly preferred. The acyl group includes, but is not limited to, formyl, acetyl, propionyl, butyryl, isobutyryl, valeryl, isovaleryl, pivaloyl, benzoyl, and other acyl groups each having about 1 to 7 carbon atoms.

The substituents $R^1$ and $R^2$ may be identical to or different from each other. The substituents $R^1$ and $R^2$ in the formula (1) may be combined to form a double bond or to form an aromatic or non-aromatic ring with the adjacent two carbon atoms. Preferred aromatic or non-aromatic rings each have about 5 to 12 members, and preferably about 6 to 10 members. The ring may be any of carbocyclic rings and heterocyclic rings, and to these rings, another ring may be condensed. Such rings include, for example, non-aromatic alicyclic rings (e.g., cyclohexane ring, and other cycloalkane rings which may have a substituent; cyclohexene ring, and other cycloalkene rings which may have a substituent; and 5-norbornene ring, and other bridged hydrocarbon rings which may have a substituent), benzene ring, naphthalene ring, and other aromatic rings (including condensed rings) which may have a substituent, and pyridine ring and other aromatic heterocyclic rings which may have a substituent. The ring is composed of an aromatic ring (a carbocyclic ring or heterocyclic ring) in many cases. The ring may have a substituent. Such substituents include, but are not limited to, alkyl groups (e.g., $C_1$–$C_4$ alkyl groups), haloalkyl groups (e.g., $C_1$–$C_4$ haloalkyl groups), aryl groups, cycloalkyl groups, hydroxyl group, alkoxy groups(e.g., $C_1$–$C_4$ alkoxy groups), carboxyl group, alkoxycarbonyl groups (e.g., $C_1$–$C_4$ alkoxy-carbonyl groups), acyl groups (e.g., $C_1$–$C_7$ acyl groups), nitro group, cyano group, sulfo group, substituted or unsubstituted amino groups, and halogen atoms.

In the formula (1), X is an oxygen atom or a hydroxyl group, and the bond between a nitrogen atom N and X is a single bond or a double bond; and Y is a single bond, a methylene group, or a carbonyl group.

One or two of heterocyclic ring containing three nitrogen atoms indicated in the formula (1) may be further formed on the substituent $R^1$ or $R^2$ or on the double bond, or aromatic or non-aromatic ring formed together by $R^1$ and $R^2$. For example, when $R^1$ or $R^2$ is an alkyl group having two or more carbon atoms, the heterocyclic ring may be formed together with adjacent two carbon atoms constituting the alkyl group. Likewise, when $R^1$ and $R^2$ are combined to form a double bond, the heterocyclic ring may be formed together with the double bond. When $R^1$ and $R^2$ are combined to form an aromatic or non-aromatic ring with the adjacent two carbon atoms, the heterocyclic ring may be formed with adjacent two carbon atoms constituting the ring.

Preferred nitrogen-containing heterocyclic compound includes a compound shown by the following formula (1a) or (1b)

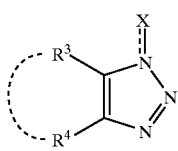

(1a)

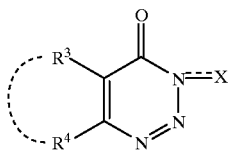

(1b)

Wherein each of $R^3$ and $R^4$ is, identical to or different from each other, a hydrogen atom, a halogen atom, an alkyl group, a haloalkyl group, an aryl group, a cycloalkyl group, a hydroxyl group, an alkoxy group, a carboxyl group, an alkoxycarbonyl group, or an acyl group, and $R^3$ and $R^4$ may be combined to form an aromatic 6-membered ring with adjacent two carbon atoms, where one or two of N-substituted triazole ring or N-substituted triazinone ring indicated in the formulae may be formed on $R^3$ or $R^4$ or on the aromatic 6-membered ring; and X is an oxygen atom or a hydroxyl group.

In the substituents $R^3$ and $R^4$, each of the halogen atom, alkyl group, haloalkyl group, aryl group, cycloalkyl group, alkoxy group, alkoxycarbonyl group, and acyl group includes groups similar to those mentioned above.

The substituents $R^3$ and $R^4$ may be combined to form an aromatic 6-membered ring with the adjacent two carbon atoms. Such aromatic 6-membered rings include, but are not limited to, benzene ring, naphthalene ring, and other carbocyclic rings; pyridine ring, quinoline ring, and other heterocyclic rings each containing a nitrogen atom.

The aromatic 6-membered ring may have a substituent. Such substituents include those similar to the substituents which the ring formed by $R^1$ and $R^2$ may have.

Typical compounds of the formula (1a) include, for example, 1-hydroxy-1H-1,2,3-triazole, 1-hydroxy-4,5-dimethyl-1H-1,2,3-triazole, 1-hydroxybenzotriazole, 5-chloro-1-hydroxybenzotriazole, 5-bromo-1-hydroxybenzotriazole, 6-chloro-1-hydroxybenzotriazole, 6-bromo-1-hydroxybenzotriazole, 4,5,6,7-tetrachloro-1-hydroxybenzotriazole, 1-hydroxy-5-methylbenzotriazole, 6-trifluoromethyl-1-hydroxybenzotriazole, 1-hydroxy-6-sulfobenzotriazole, 1-hydroxy-6-nitrobenzotriazole, 5-methoxy-1-hydroxybenzotriazole, and 1-hydroxypyrido [3,2-d]-1H-1,2,3-triazole.

Typical compounds of the formula (1b) include, for example, 1,6-dihydro-1-hydroxy-6-oxo-1,2,3-triazine, 1,6-dihydro-1-hydroxy-4,5-dimethyl-6-oxo-1,2,3-triazine, 3,4-dihydro-3-hydroxy-4-oxo-1,2,3-benzotriazine, 3,4-dihydro-3-hydroxy-6-iodo-4-oxo-1,2,3-benzotriazine, 3,4-dihydro-3-hydroxy-6-methyl-4-oxo-1,2,3-benzotriazine, 7-chloro-3,4-dihydro-3-hydroxy-4-oxo-1,2,3-benzotriazine, 3,4-dihydro-3-hydroxy-7-nitro-4-oxo-1,2,3-benzotriazine, 3,4-dihydro-3-hydroxy-6,7-dimethyl-4-oxo-1,2,3-benzotriazine, 3,4-dihydro-3-hydroxy-6,7-dimethoxy-4-oxo-1,2,3-benzotriazine, and 3,4-dihydro-3-hydroxy-4-oxonaphtho[2,3-d]-1,2,3-triazine.

The nitrogen-containing heterocyclic compounds of the formula (1) can be obtained by a conventional or known process. For example, of the nitrogen-containing heterocyclic compounds of the formula (1), the compound of the formula (1a) can be obtained by allowing a β-halogenonitro compound shown by the following formula (2):

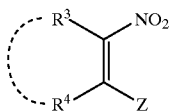

(2)

wherein Z is a halogen atom; and $R^3$ and $R^4$ have the same meanings as defined above, to react with hydrazine in an alcohol such as heptanol at a temperature of about 50° C. to 160° C. (refer to, for example, Japanese Unexamined Patent Application Publication No. 55-149266).

The compound of the formula (1b) can be obtained, for example, by a process including the steps of allowing a β-amino acid compound shown by the following formula (3):

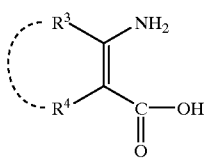

(3)

wherein $R^3$ and $R^4$ have the same meanings as defined above, to react with thionyl chloride, for example, under reflux of benzene, allowing the reaction mixture to further react with o-(trimethylsilyl)hydroxylamine at room temperature, adding hydrochloric acid to the resulting mixture, and adding a sodium nitrite aqueous solution to the mixture at a temperature of, for example, 4° C. or below (e.g., Synthesis 1990, 1008).

Each of the nitrogen-containing heterocyclic compounds of the formula (1) can be used alone or in combination. The amount of the compound of the formula (1) can be selected within a wide range, and is, for example, about 0.0000001 to 1 mole, preferably about 0.00001 to 0.5 mole, and more preferably about 0.0001 to 0.4 mole, relative to 1 mole of the organic substrate.

[Promoter (Co-catalyst)]

According to the invention, a promoter (co-catalyst) can be used in combination with the nitrogen-containing heterocyclic compound. Such promoters include, for example, (i) metallic compounds. The combination use of the nitrogen-containing heterocyclic compound with a metallic compound can improve the rate and selectivity of the reaction.

Metallic elements constituting the metallic compounds (i) are not limited and are often metallic elements of the Groups 2 to 15 of the Periodic Table of Elements. The term "metallic element" as used herein also includes boron B. Examples of the metallic elements include, of the Periodic Table of Elements, Group 2 elements (e.g., Mg, Ca, Sr, Ba), Groups 3 elements (e.g., Sc, lanthanoid elements, actinoid elements), Group 4 elements (e.g., Ti, Zr, Hf), Group 5 elements (e.g., V), Group 6 elements (e.g., Cr, Mo, W), Group 7 elements (e.g., Mn), Group 8 elements (e.g., Fe, Ru), Group 9 elements (e.g., Co, Rh), Group 10 elements (e.g., Ni, Pd, Pt), Group 11 elements (e.g., Cu), Group 12 elements (e.g., Zn), Groups 13 elements (e.g. B, Al, In), Group 14 elements (e.g., Sn, Pb), and Group 15 element s (e.g., Sb, Bi). Preferred metallic elements include transition metal elements (elements of Groups 3 to 12 of the Periodic Table of Elements). Among them, elements of the Groups 5 to 11 of the Periodic Table of Elements are preferred, of which elements of Groups 5 to 9 are typically preferred. Especially, V, Mo, Mn, and Co can be advantageously used. The valency of the metallic element is not particularly limited, and is about 0 to 6 in many cases.

Such metallic compounds include, but are not limited to, elementary substances, hydroxides, oxides (including complex oxides), halides (fluorides, chlorides, bromides, and iodides), salts of oxoacids (e.g., nitrates, sulfates, phosphates, borates, and carbonates), salts of isopolyacids, salts of heteropolyacids, and other inorganic compounds of the aforementioned metallic elements; salts of organic acids (e.g., salts of acetic acid, propionic acid, hydrocyanic acid, naphthenic acid, or stearic acid), complexes, and other organic compounds of the metallic elements. Ligands for constituting the complexes include OH (hydroxo), alkoxy (e.g., methoxy, ethoxy, propoxy, and butoxy), acyl (e.g., acetyl and propionyl). alkoxycarbonyl groups (e.g., methoxycarbonyl and ethoxycarbonyl), acetylacetonato, cyclopentadienyl group, halogen atoms (e.g., chlorine and bromine atoms), CO, CN, oxygen atom, $H_2O$ (aquo), phosphines (triphenylphosphine and other triarylphosphines), and other phosphorus compounds, $NH_3$ (ammine), NO, $NO_2$ (nitro), $NO_3$ (nitrato), ethylenediamine, diethylenetriamine, pyridine, phenanthroline, and other nitrogen-containing compounds, and $BH_4$.

Concrete examples of the metallic compounds include, by taking cobalt compounds as example, cobalt hydroxide, cobalt oxide, cobalt chloride, cobalt bromide, cobalt nitrate, cobalt sulfate, cobalt phosphate, and other inorganic compounds; cobalt acetate, cobalt naphthenate, cobalt stearate, and other salts of organic acids; acetylacetonatocobalt, and other complexes, and other divalent or trivalent cobalt compounds. Illustrative vanadium compounds include vanadium hydroxide, vanadium oxide, vanadium chloride, vanadyl chloride, vanadium sulfate, vanadyl sulfate, sodium vanadate, and other inorganic compounds; acetylacetonatovanadium, vanadyl acetylacetonato, and other complexes, and other vanadium compounds having a valency of 2 to 5. Illustrative molybdenum compounds include molybdenum hydroxide, molybdenum oxide, molybdenum chloride, molybdenum bromide, molybdenum sulfide, molybdic acid or its salts, phosphomolybdic acid or its salts, silicomolybdic acid or its salts, and other inorganic compounds; molybdenum carbonyl, bis(acetylacetonato) dioxomolybdenum, chlorotricarbonyl (η-cyclopentadienyl) molybdenum, dibromobis (η-cylopentadienylmolybdenum, and other complexes, and other molybdenum compounds having a valency of 0 to 6. Examples of compounds of the other metallic elements include compounds corresponding to the above-mentioned cobalt, vanadium or molybdenum compounds. Each of these metallic compounds can be used alone or in combination.

The amount of the metallic compound is, for example, about 0.001 to 0.1 mole, and preferably about 0.005 to 0.08 mole, relative to 1 mole of the nitrogen-containing heterocyclic compound of the formula (1).

In the invention, (ii) the following organic salts can be also used as promoters. The organic salts (ii) are each composed of a polyatomic cation or a polyatomic anion and its counter ion, the polyatomic cation or anion contains a Group 15 or Group 16 element of the Periodic Table of Elements, and the element is combined with at least one organic group. The use of the organic salts as promoters can improve the rate and selectivity of the reaction.

In the organic salts, the Group 15 elements of the Periodic Table of Elements include N, P, As, Sb, and Bi, and the Group 16 elements of the Periodic Table of Elements include, for example, O, S, Se and Te. Preferred elements are N, P, As, Sb, and S, of which N, P, and S are typically preferred.

The organic groups to be combined with atoms of the elements include, for example, hydrocarbon groups which may have a substituent, and substituted oxy groups. The hydrocarbon groups include, but are not limited to, methyl, ethyl, propyl, isopropyl, butyl, isobutyl, s-butyl, t-butyl, pentyl, hexyl, octyl, decyl, tetradecyl, hexadecyl, octadecyl, allyl, and other straight- or branched-chain aliphatic hydrocarbon groups (alkyl groups, alkenyl groups and alkynyl groups) each having about 1 to 30 carbon atoms (preferably about 1 to 20 carbon atoms); cyclopentyl, cyclohexyl, and other alicyclic hydrocarbon groups each having about 3 to 8 carbon atoms; and phenyl, naphthyl, and other aromatic hydrocarbon groups each having about 6 to 14 carbon atoms. Substituents which the hydrocarbon groups may have include, but are not limited to, halogen atoms, oxo group, hydroxyl group, substituted oxy groups (e.g., alkoxy groups, aryloxy groups, and acyloxy groups), carboxyl group, substituted oxycarbonyl groups, substituted or unsubstituted carbamoyl groups, cyano group, nitro group, substituted or unsubstituted amino groups, alkyl groups (e.g.,methyl, ethyl, and other $C_1$–$C_4$ alkyl groups), cycloalkyl groups, aryl groups (e.g., phenyl and naphthyl groups), and heterocyclic groups. Preferred hydrocarbon groups include, for example, alkyl groups each having about 1 to 30 carbon atoms, and aromatic hydrocarbon groups (especially, phenyl or naphthyl group) each having about 6 to 14 carbon atoms. The substituted oxy groups include, for example, alkoxy groups, aryloxy groups and aralkyloxy groups.

Typical examples of the organic salts are organic ammonium salts, organic phosphonium salts, organic sulfonium salts, and other organic onium salts. Concrete examples of organic ammonium salts include tetramethylammonium chloride, tetraethylammonium chloride, tetrabutylammonium chloride, tetrahexylammonium chloride, trioctylmethylammonium chloride, triethylphenylammonium chloride, tributyl(hexadecyl)ammonium chloride, di(octadecyl)dimethylammonium chloride, and other quaternary ammonium chlorides, and corresponding quaternary ammonium bromides, and other quaternary ammonium salts each having four hydrocarbon groups bonded to its nitrogen atom; dimethylpiperidinium chloride, hexadecylpyridinium chloride, methylquinolinium chloride, and other cyclic quaternary ammonium salts. Practical examples of the organic phosphonium salts include tetramethylphosphonium chloride, tetrabutylphosphonium chloride, tributyl (hexadecyl)phosphonium chloride, triethylphenylphosphonium chloride, and other quaternary phosphonium chlorides, and corresponding quaternary phosphonium bromides, and other quaternary phosphonium salts each having four hydrocarbon groups bonded to its phosphorus atom. Concrete examples of the organic sulfonium salts include triethylsulfonium iodide, ethyldiphenylsulfonium iodide, and other sulfonium salts each having three hydrocarbon groups bonded to its sulfur atom.

The organic salts also include, for example, methanesulfonates, ethanesulfonates, octanesulfonates, dodecanesulfonates, and other alkyl-sulfonates (e.g., $C_6$–$C_{18}$ alkyl-sulfonates); benzenesulfonates, p-toluenesulfonates, naphthalenesulfonates, decylbenzenesulfonates, dodecylbenzenesulfonates, and other aryl-sulfonates (e.g., $C_6$–$C_{18}$ alkyl-arylsulfonates) which may be substituted with an alkyl group, sulfonic acid type ion exchange resins (ion exchangers); and phosphonic acid type ion exchange resins (ion exchangers).

The amount of the organic salt is, for example, about 0.001 to 0.1 mole, and preferably about 0.005 to 0.08 mole, relative to 1 mole of the nitrogen-containing heterocyclic compound.

For use as promoters in the invention, (iii) strong acids can also be employed. The combination use of the nitrogen-containing heterocyclic compound with a strong acid concurrently with the use of oxygen as the oxygen-atom-containing reactant can efficiently introduce an oxo group into a methylene carbon atom (secondary carbon atom) of the organic substrate.

The strong acids (iii) include, for example, compounds each having a pKa of 2 or less (at 25° C.) The pKa of the strong acids is preferably about −15 to 2, and more preferably about −10 to 0. Such strong acids include, but are not limited to, hydrogen halides (hydrogen fluoride, hydrogen chloride, hydrogen bromide, and hydrogen iodide), hydrohalogenic acids (hydrofluoric acid, hydrochloric acid, hydrobromic acid, and hydroidodic acid), oxoacids (e.g., sulfuric acid, nitric acid, phosphoric acid, chromic acid and other metallic acids, chloric acid, and other halogenic acids), super strong acids (e.g., $ClSO_3H$, $H_2SO_4$—$SO_3$, $FSO_3H$, $FSO_3H$—$SO_3$, $FSO_3H$—$SbF_5$, and $HF$—$SbF_5$), heteropolyacids (e.g., silicomolybdic acid, silicotungstic acid, phosphomolybdic acid, phosphotungstic acid, phosphovanadomolybdic acid, and phosphovanadotungstic acid), and sulfonic acids (e.g., methanesulfonic acid, trifluoromethanesulfonic acid, benzenesulfonic acid, p-toluenesulfonic acid, and naphthalenesulfonic acid). Preferred strong acids include inorganic acids such as hydrogen halides, hydrohalogenic acids, sulfuric acid, and heteropolyacids. Each of these strong acids can be used alone or in combination. The amount of the strong acid is, for example, about 0.001 to 3 moles, and more preferably about 0.1 to 1 mole, relative to 1 mole of the nitrogen-containing heterocyclic compound.

According to the invention, (iv) compounds each having a carbonyl group combined with an electron attracting group can be employed as promoters. The combination use of such a compound with the nitrogen-containing heterocyclic compound can markedly increase a reaction rate when the organic substrate is oxidized in the coexistence of another substrate (particularly, a primary or secondary alcohol) (co-oxidation) or when a Baeyer-Villiger type reaction mentioned below is performed.

In the compounds (iv) each having a carbonyl group combined with an electron attracting group, the electron attracting group includes, but is not limited to, phenyl; fluoromethyl, trifluoromethyl, tetrafluoroethyl, fluorophenyl, pentafluorophenyl, and other hydrocarbon groups each substituted with a fluorine atom. Practical examples of the compounds (iv) include hexafluoroacetone, trifluoroacetic acid, pentafluorophenyl methyl ketone, pentafluorophenyl trifluromethyl ketone, and benzoic acid. The amount of this compound is, for example, about 0.0001 to 1 mole, preferably about 0.001 to 0.7 mole, and more preferably about 0.01 to 0.5 mole, relative to 1 mole of the organic substrate.

Either in the identical category or different categories, each of the promoters (i) to (iv) can be used alone or in combination. For example, one or more of the metallic compounds (i) can be used in combination with one or more of the compounds (iv) each having a carbonyl group combined with an electron attracting group.

According to the invention, a reaction system may include a radical generator or a radical reaction accelerator. Such components include, but are not limited to, halogens (e.g., chlorine, and bromine), peracids (e.g., peracetic acid and m-chloroperbenzoic acid), and peroxides (e.g., hydrogen peroxide, t-butyl hydroperoxide (TBHP), and other hydroperoxides). The existence of such a component in the system can enhance a reaction in some cases. The amount of the aforementioned component is, for example, about 0.001 to 0.1 mole relative to 1 mole of the nitrogen-containing heterocyclic compound.

[Oxygen-atom-containing Reactant]

The oxygen-atom-containing reactants (reacting agents) includes a variety of reactants each containing an oxygen atom (e.g., oxygen-atom-containing gases). Such reactants include, for example, oxygen, carbon monoxide, nitrogen oxides, and sulfur oxides. Each of these oxygen-atom-containing reactants can be used alone or in combination.

The oxygen may be any of molecular oxygen and active oxygen. Such molecular oxygen includes, but is not limited to, pure oxygen; oxygen diluted with an inert gas such as nitrogen, helium, argon, or carbon dioxide; and air. The molecular oxygen is often employed as the oxygen.

The carbon monoxide may be pure carbon monoxide or carbon monoxide diluted with an inert gas.

The nitrogen oxides include, for example, $N_2O_3$, $N_2O$, NO, and $NO_2$. These nitrogen oxides such as nitrogen dioxide $NO_2$ can be used in combination with oxygen. In this connection, $N_2O_3$ can be easily obtained upon a reaction of $N_2O$ and/or NO with oxygen. More specifically, $N_2O_3$ can be prepared by introducing nitrogen monoxide and oxygen into a reactor to yield a blue liquid $N_2O_3$.

The sulfur oxides include, for example, $SO_2$ and $SO_3$. These sulfur oxides such as $SO_2$ can be employed in combination with oxygen.

By appropriately selecting the oxygen-atom-containing reactant, the organic substrate can be, for example, oxidized, carboxylated, nitrated, or sulfonated. Some combinations of the organic substrates can yield a carbon-carbon bond.

[Oxidation]

An organic substrate is allowed to react with oxygen in the presence of the catalyst to yield a corresponding oxidation product.

A wide variety of compounds can be used as the organic substrate. For example, at least one compound selected from the following groups can be used as the organic substrate: (a) primary or secondary alcohols, (b) compounds each having a carbon-hydrogen bond at the adjacent position to an unsaturated bond, (c) compounds each having a methine carbon atom, (d) cycloalkanes, (e) non-aromatic heterocyclic compounds each having a carbon-hydrogen bond at the adjacent position to a hetero atom, (f) conjugated compounds, (g) aromatic hydrocarbons, (h) thiols, (i) ethers, (j) sulfides, (k) aldehydes or thioaldehydes, (l) amines, (m) compounds each having a non-aromatic ethylenic bond, (n) ketones, and (o) polymers. These compounds may have a variety of substituents. Such substituents include, but are not limited to, halogen atoms, oxo group, hydroxyl group, mercapto group, substituted oxy groups (e.g., alkoxy groups, aryloxy groups, and acyloxy groups), substituted thio groups, carboxyl group, substituted oxycarbonyl group, substituted or unsubstituted carbamoyl groups, cyano group, nitro group, substituted or unsubstituted amino groups, alkyl groups, alkenyl groups, alkynyl groups, cycloalkyl groups, cycloalkenyl groups, aryl groups (e.g., phenyl and naphthyl groups), aralkyl groups, and heterocyclic groups. In many cases, the co-oxidation of two or more types of organic substrates can markedly improve the rate of oxidation as compared with the oxidation of a single organic substrate alone.

(a) Primary or secondary alcohols

The primary or secondary alcohols (a) include a wide variety of alcohols. These alcohols may be whichever of monohydric, dihydric and polyhydric alcohols. Such primary alcohols include, but are not limited to, methanol, ethanol, 1-propanol, 1-butanol, 1-decanol, ethylene glycol, and other saturated or unsaturated aliphatic primary alcohols; cyclopentylmethyl alcohol, cyclohexylmethyl alcohol, and other saturated or unsaturated alicyclic primary alcohols; benzyl alcohol, 2-phenylethyl alcohol, and other aromatic primary alcohols; and 2-hydroxymethylpyridine, and other heterocyclic alcohols. The secondary alcohols include, but are not limited to, 2-propanol, s-butyl alcohol, and other saturated or unsaturated aliphatic secondary alcohols; cyclopentanol, cyclohexanol, and other saturated or unsaturated alicyclic secondary alcohols; 1-phenylethanol, 1-phenylpropanol, 1-phenylmethylethanol, diphenylmethanol, and other aromatic secondary alcohols; and 1-(2-pyridyl)ethanol, and other heterocyclic secondary alcohols. Preferred primary or secondary alcohols (a) include secondary alcohols such as s-butyl alcohol, and other aliphatic secondary alcohols, cyclohexanol, and other alicyclic secondary alcohols, 1-phenylethanol, and other aromatic secondary alcohols. Each of these alcohols (a) can be used alone or in combination.

The oxidation of such a primary or secondary alcohol with oxygen in the presence of the catalyst yields a corresponding aldehyde or ketone, or carboxylic acid. The use of cyclohexanol or another alicyclic secondary alcohol as a material yields a dicarboxylic acid (e.g., adipic acid corresponding to cyclohexanol) in addition to a corresponding cyclic ketone (e.g., cyclohexanone corresponding to cyclohexanol). When a 1,2-diol is oxidized, two carbon atoms to which hydroxyl groups are bonded undergo oxidative cleavage to yield a corresponding carboxylic acid.

(b) Compounds each having a carbon-hydrogen bond at the adjacent position to an unsaturated bond The compounds (b) each having a carbon-hydrogen bond at the adjacent position to an unsaturated bond include, for example, (b1) aromatic compounds each having a methyl group or methylene group at the adjacent position to its aromatic ring (a benzyl position), and (b2) non-aromatic compounds each having a methyl group or methylene group at the adjacent position to an unsaturated bond (e.g., a carbon-carbon triple bond, a carbon-oxygen double bond). In the aromatic compounds (b1), the aromatic ring may be any of aromatic hydrocarbon rings or aromatic heterocyclic rings. The methylene group at the adjacent position to an aromatic ring may be a methylene group constituting a non-aromatic ring condensed to the aromatic ring. The aromatic compounds each having a methyl group at the adjacent position to an aromatic ring include, for example, aromatic hydrocarbons (e.g., toluene, xylene, and methylnaphthalene) each having about one to six methyl groups substituted on an aromatic ring, and heterocyclic compounds (e.g., 4-methylpyridine) each having about one to six methyl groups substituted on a heterocyclic ring. The aromatic compounds each having a methylene group at the adjacent position to an aromatic ring include, but are not limited to, aromatic hydrocarbons (e.g., ethylbenzene, propylbenzene, and diphenylmethane) each having an alkyl group or substituted alkyl group having two or more carbon atoms, aromatic heterocyclic compounds (e.g., 4-ethylpyridine) each having an alkyl group or substituted alkyl group having 2 or more carbon atoms, and compounds (e.g., dihydronaphthalene, indene, indan, tetralin, fluorene, acenaphthene, phenalene, and xanthene) each having a non-aromatic ring condensed to an aromatic ring and having a methylene group in the non-aromatic ring at the adjacent position to the aromatic ring.

The non-aromatic compounds (b2) each having a methyl group or methylene group at the adjacent position to an unsaturated bond include, but are not limited to, (b2-1) chain unsaturated hydrocarbons each having a methyl group or methylene group at the adjacent position to a carbon-carbon triple bond, and (b2-2) compounds each having a methyl group or methylene group at the adjacent position to a carbonyl group. Illustrative chain unsaturated hydrocarbons (b2-1) are methylacetylene, and other alkynes each having about 3 to 20 carbon atoms. The compounds (b2-2) include, for example, carboxylic acids or derivatives thereof (e.g., malonic acid, succinic acid, glutaric acid, and esters of these acids).

When the compound (b) having a carbon-hydrogen bond at the adjacent position to an unsaturated bond is oxidized with oxygen in the presence of the catalyst, a hydroxyl group or oxo group is introduced at the adjacent position to the unsaturated bond to yield a corresponding alcohol, aldehyde or ketone.

(c) Compounds each having a methine carbon atom

The compounds (c) each having a methine carbon atom (or a tertiary carbon atom) include (c1) cyclic compounds each having a methine group (i.e., a methine carbon-hydrogen bond) as a constitutive unit of its ring, and (c2) chain compounds each having a methine carbon atom. The cyclic compounds (c1) include, for example, (c1-1) bridged cyclic compounds each having at least one methine group, and (c1-2) non-aromatic cyclic compounds (e.g., alicyclic hydrocarbons) each having a hydrocarbon group bonded to its ring. The bridged cyclic compounds also include compounds in which two rings commonly possess two carbon atoms, such as hydrogenated products of condensed polycyclic aromatic hydrocarbons.

Such bridged cyclic compounds (c1-1) include, but are not limited to, decalin, bicyclo[2.2.2]octane, pinane, pinene, bornane, norbornane, norbornene, camphor, endotricyclo[5.2.1.0$^{2,6}$]decane, adamantane, 1-adamantanol, perhydroanthracene, and other bridged cyclic hydrocarbons or bridged heterocyclic compounds each having two to four rings, and derivatives thereof. These bridged cyclic compounds each have a methine carbon atom at a bridgehead position (corresponding to a junction position when two rings commonly possess two atoms). The non-aromatic cyclic compounds (c1-2) each having a hydrocarbon group bonded to its ring include, for example, 1-methylcyclopentane, 1-methylcyclohexane, and other alicyclic hydrocarbons each having a hydrocarbon group (e.g., an alkyl group) bonded to its ring, and derivatives thereof. The non-aromatic cyclic compounds (c1-2) each having a hydrocarbon group bonded to its ring each have a methine carbon atom at a junction position between its ring and the hydrocarbon group.

The chain compounds (c2) each having a methine carbon atom include, but are not limited to, chain hydrocarbons each having a tertiary carbon atom, such as isobutane, isopentane, isohexane, and 3-methylpentane, and other aliphatic hydrocarbons, and derivatives thereof.

The oxidation of the compound (c) having a methine carbon atom in the presence of the catalyst introduces a hydroxyl group into the methine carbon atom to yield a corresponding alcohol.

(d) Cycloalkanes

Illustrative cycloalkanes (d) are, for example, cyclopentane, cyclohexane, cycloheptane, cyclooctane, cyclododecane, cyclotetradecane, and other cycloalkanes each having about 5 to 30 members, and derivatives thereof.

The oxidation of the cycloalkane (d) with oxygen in the presence of the catalyst yields a corresponding cycloalkanone (e.g., cyclohexanone corresponding to cyclohexane) or a dicarboxylic acid (e.g., adipic acid corresponding to cyclohexane) which is formed by further oxidizing and cleaving the cycloalkanone.

(e) Non-aromatic heterocyclic compounds each having a carbon-hydrogen bond at the adjacent position to a hetero atom In the non-aromatic heterocyclic compounds (e) each having a carbon-hydrogen bond at the adjacent position to a hetero atom, non-aromatic heterocyclic rings include, for example, heterocyclic rings each having at least one hetero atom selected from a nitrogen atom, an oxygen atom and a sulfur atom. To each of the heterocyclic rings, one or two benzene rings, cyclohexane rings, pyridine rings or other aromatic or non-aromatic rings may be condensed. Examples of the heterocyclic rings include dihydrofuran, tetrahydrofuran, pyran, dihydropyran, tetrahydropyran, pyrrolidine, piperidine, piperazine, morpholine, indoline, chroman, and isochroman.

When the non-aromatic heterocyclic compound (e) having a carbon-hydrogen bond at the adjacent position to a hetero atom is oxidized with oxygen in the presence of the catalyst, a carbon atom at the adjacent position to the hetero atom is oxidized and a hydroxyl group or an oxo group is introduced or the bond is cleaved to yield a dicarboxylic acid. For example, the oxidation of tetrahydropyran yields, for example, δ-valerolactone, glutaric acid, or glutaric anhydride.

(f) Conjugated compounds

Such conjugated compounds (f) include, but are not limited to, conjugated dienes (f1), α,β-unsaturated nitriles (f2), and α,β-unsaturated carboxylic acids or derivatives thereof (e.g., esters, amides, and acid anhydrides). Such conjugated dienes (f1) include, for example, butadiene and isoprene. The conjugated dienes (f1) also include compounds in which a double bond and a triple bond are conjugated, such as vinyl acetylene. The α,β-unsaturated nitriles (f2) include, for example, (meth)acrylonitrile. Illustrative α,β-unsaturated carboxylic acids or derivatives thereof are (meth)acrylic acid; methyl (meth)acrylate, ethyl (meth)acrylate, and other (meth)acrylic esters; and (meth)acrylamide or derivatives thereof.

The oxidation of the conjugated diene (f1) with oxygen in the presence of the catalyst yields a corresponding alkene-diol. The oxidation of the α,β-unsaturated nitrile (f2) or α,β-unsaturated carboxylic acid or a derivative thereof with oxygen in the presence of the catalyst yields, for example, propionitrile or propionic acid derivative having two hydroxyl groups or alkoxy groups (when oxidized in the presence of an alcohol) bonded at the β-position. More specifically, when acrylonitrile is oxidized in methanol, for example, 1,1-dimethoxypropionitrile is formed. Likewise, when methyl acrylate is oxidized in methanol, for example, methyl 1,1-dimethoxypropionate is formed.

(g) Aromatic hydrocarbons

The aromatic hydrocarbons (g) include, for example, benzene, naphthalene, acenaphthylene, phenanthrene, anthracene, naphthacene, and other aromatic compounds each having at least one benzene ring, of which condensed polycyclic aromatic compounds having at least plural benzene rings (e.g., two to ten benzene rings) condensed thereto are preferred. These aromatic hydrocarbons may each have one or more substituents. Practical examples of such aromatic compounds each having a substituent include 2-chloronaphthalene, 2-methoxynaphthalene, 1-methylnaphthalene, 2-methylnaphthalene, 2-methylanthracene, 2-t-butylanthracene, 2-carboxyanthracene, 2-ethoxycarbonylanthracene, 2-cyanoanthracene, 2-nitroanthracene, and 2-methylpentalene. To each of the benzene rings, a non-aromatic carbocyclic ring, an aromatic heterocyclic ring, or a non-aromatic heterocyclic ring may be condensed.

The oxidation of the aromatic hydrocarbon (g) with oxygen in the presence of the catalyst yields a corresponding quinone (e.g., anthraquinone corresponding to anthracene). In this case, the production rate of the quinone can be markedly improved by subjecting the substrate to co-oxidation in the co-existence of the primary or secondary alcohol (a) (e.g., cyclohexanol) or the compound (b) (e.g., fluorene) having a carbon-hydrogen bond at the adjacent position to an unsaturated bond.

(h) Thiols

The thiols (h) include, but are not limited to, methanethiol, ethanethiol, and other aliphatic thiols; cyclopentanethiol, and other alicyclic thiols; and phenylmethanethiol, and other aromatic thiols.

(i) Ethers

The ethers (i) include, but are not limited to, diethyl ether, dipropyl ether, and other aliphatic ethers; and anisole, benzyl methyl ether, dibenzyl ether, and other aromatic ethers.

When the ether (i) is oxidized with oxygen in the presence of the catalyst, a carbon atom at the adjacent position to an oxygen atom constituting the ether is oxidized to yield a corresponding ester or acid anhydride (e.g., methyl benzoic acid is formed from benzyl methyl ether).

(j) Sulfides

The sulfides (j) include, but are not limited to, diethyl sulfide, dipropyl sulfide, and other aliphatic sulfides; and methyl phenyl sulfide, ethyl phenyl sulfide, and other aromatic sulfides.

The oxidation of the sulfide (j) with oxygen in the presence of the catalyst yields a corresponding sulfoxide or sulfone (e.g., methyl phenyl sulfoxide and methyl phenyl sulfone are formed from methyl phenyl sulfide). In this case, the production rate of the sulfoxide or sulfone can be markedly improved by subjecting the substrate to co-oxidation in the coexistence of, for example, the primary or secondary alcohol (a) (e.g., cyclohexanol).

(k) Aldehydes or thioaldehydes

Examples of the aldehydes are acetaldehyde, propionaldehyde, hexanal, decanal, succinaldehyde, glutaraldehyde, adipaldehyde, and other aliphatic aldehydes; formylcyclohexane, and other alicyclic aldehydes; benzaldehyde, nitrobenzaldehyde, cinnamaldehyde, salicylaldehyde, anisaldehyde, phthalaldehyde, isophthalaldehyde, terephthalaldehyde, and other aromatic aldehydes; and furfural, nicotinic aldehyde, and other heterocyclic aldehydes. The thioaldehydes include thioaldehydes corresponding to the aforementioned aldehydes.

The oxidation of the aldehyde with oxygen in the presence of the catalyst yields, for example, a corresponding carboxylic acid.

(l) Amines

The illustrative amines (l) are primary or secondary amines such as methylamine, ethylamine, propylamine, butylamine, dimethylamine, diethylamine, ethylenediamine, hydroxylamine, ethanolamine, and other aliphatic amines; cyclohexylamine, and other alicyclic amines; benzylamine, toluidine, and other aromatic amines.

(m) Compounds each having a non-aromatic ethylenic bond

The compounds (m) each having a non-aromatic ethylenic bond include, but are not limited to, propene, 1-butene, 2-butene, 1-hexene, 2-hexene, 1-octene, 2-octene, and other chain hydrocarbons each having an ethylenic bond; cyclopentene, cyclohexene, cyclooctene, cyclodecene, and other compounds each having a cycloalkene ring; bicyclo [2.2.1]hept-2-ene, and other unsaturated bridged cyclic hydrocarbons; and 3,6-dihydro-2H-pyran, and other heterocyclic compounds each having a non-aromatic ethylenic bond as a component of a ring.

The oxidation of the compound (m) having a non-aromatic ethylenic bond with oxygen in the presence of the catalyst yields a corresponding epoxy compound (e.g., 2,3-epoxyoctane is formed from 2-octene, and cyclooctene oxide is formed from cyclooctene). In this case, the production rate of the epoxy compound can be markedly improved by subjecting the substrate to co-oxidation in the co-existence of, for example, the primary or secondary alcohol (a) (e.g., benzhydrol) or the compound (b) having a carbon-hydrogen bond at the adjacent position to an unsaturated bond (e.g., tetralin).

(n) Ketones

The ketones (n) include, but are not limited to, methyl ethyl ketone, methyl isopropyl ketone, methyl decyl ketone, and other chain ketones; cyclopentanone, cyclohexanone, cycloheptanone, 2-adamantanone, and other cyclic ketones.

The oxidation of the ketone (n) with oxygen in the presence of the catalyst proceeds a Baeyer-Villiger type reaction to yield a corresponding ester from a chain ketone or to yield a corresponding lactone from a cyclic ketone. For example, $\epsilon$-caprolactone is formed from cyclohexanone. The use of a secondary alcohol as a material yields, via a corresponding ketone, an ester or lactone.

In this case, the production rate of the ester or lactone can be markedly improved by subjecting the substrate to co-oxidation in the co-existence of, for example, the primary or secondary alcohol (a) (e.g., benzhydrol) or the compound (b) having a carbon-hydrogen bond at the adjacent position to an unsaturated bond (e.g., tetralin).

(o) Polymers

The polymers (o) include a variety of polymers each having a primary, secondary, or tertiary carbon atom in a principal chain or side chain. Such polymers include, but are not limited to, polyethylenes (e.g., low density polyethylene, linear low density polyethylene, and metallocene type polyethylene), ethylene copolymers (e.g., ethylene-vinyl acetate copolymers, ethylene-acrylate copolymers, ethylene-methacrylate copolymers, ethylene-acrylic acid copolymers, ethylene-methacrylic acid copolymers, and ionomers), polypropylene, ethylene-propylene copolymers, poly-1-butene, poly(4-methylpentene) (TPX), polyisobutylene, and other olefinic resins; polybutadiene, polyisoprene, butadiene-styrene copolymers, butadiene-propylene copolymers, butadiene-acrylonitrile copolymers, isoprene-styrene copolymers, and other diene resins; ring-opened polymers of cyclic olefins (or hydrogenated products thereof) such as cycloolefins (e.g., cyclobutene, cyclopentene, cycloheptene, cyclooctene, 3-methylcyclooctene, cyclooctadiene, cyclodecene, 3-methylcyclodecene, cyclododecene, and cyclododecatriene), norbornene derivatives, tetracyclododecene, products of a Diels-Alder reaction of dicyclopentadiene with a (meth)acrylic ester; copolymers of the cyclic olefins with olefins such as ethylene; polystyrene, styrene-acrylonitrile copolymers, styrene-acrylonitrilebutadiene copolymers, poly(α-methylstyrene), and other polymers each comprising an aromatic vinyl compound as a monomeric component; polymers each including, as a monomeric component, an alicyclic vinyl compound such as vinylcyclohexane, vinylcyclohexene, vinyladamantane, vinylnorbornane, and vinylnorbornene; vinyl chloride resins; vinylidene chloride resins; vinyl acetate resins; cellulosic resins; polyethers; a variety of polyesters formed by polycondensation of a dibasic acid with a glycol; polyamides; acrylic resins including, as a monomeric component, an acrylic compound such as (meth)acrylic esters. The ring-opened polymers of cyclic olefins can be obtained by metathesis polymerization.

The polymers should preferably have a secondary or tertiary carbon atoms, and more preferably have a tertiary carbon atoms.

When the polymer (o) is oxidized with oxygen in the presence of the catalyst, a hydroxyl group or an oxo group is introduced into a primary carbon atom (e.g., a methyl carbon atom at the benzyl or allyl position), a secondary carbon atom (e.g., a methylene carbon atom at the benzyl or allyl position; or a methylene carbon atom constituting a non-aromatic carbocyclic ring) or a tertiary carbon atom (e.g., a methine carbon atom in a branched alkyl group or alkylene group; or a methine carbon atom at a junction position or bridgehead position of a polycyclic group) of the polymer molecule. A carboxyl group may be formed under some conditions.

When a plastic molded article comprising the polymer is oxidized with oxygen in the presence of the catalyst, polymer molecules on the surface of the plastic molded article are oxidized to yield a surface-modified plastic molded article.

The amount of oxygen in oxidation of the organic substrate can be selected within a range depending on the types of the organic substrate and target compound and is generally equal to or more than 0.5 mole (e.g., equal to or more than 1 mole), and preferably about 1 to 100 moles, relative to 1 mole of the organic substrate. Molecular oxygen in excess moles to the organic substrate is often used.

In the oxidation, nitrogen monoxide can be used as an oxidizing agent instead of oxygen. For example, the contact of the ether with nitrogen monoxide in the presence of the catalyst yields a corresponding acetal compound or carbonyl compound. Specifically, phthalan yields, for example, phthalaldehyde, and benzyl methyl ether yields, for example, benzaldehyde and methyl benzoate.

The oxidation is generally performed in an organic solvent. Such organic solvents include, but are not limited to, acetic acid, propionic acid, and other organic acids; acetonitrile, propionitrile, benzonitrile, and other nitrites; formamide, acetamide, dimethylformamide (DMF), dimethylacetamide, and other amides; hexane, octane, and other aliphatic hydrocarbons; chloroform, dichloromethane, dichloroethane, carbon tetrachloride, chlorobenzene, trifluoromethylbenzene, and other halogenated hydrocarbons; nitrobenzene, nitromethane, nitroethane, and other nitro compounds; ethyl acetate, butyl acetate, and other esters; and mixtures of these solvents. In may cases, acetic acid and other organic acids, acetonitrile, benzonitrile, and other nitriles, trifluoromethylbenzene, and other halogenated hydrocarbons, ethyl acetate and other esters are used as the solvent.

A reaction temperature can be selected depending on the types of the organic substrate and target compound, and is, for example, about 0° C. to 300° C., preferably about 20° C. to 200° C., and more preferably about 30° C. to 150° C. The reaction is usually performed at a temperature of about 40° C. to 100° C. The reaction can be performed at atmospheric pressure or under a pressure (under a load). When the reaction is conducted under a pressure, the pressure is usually about 1 to 100 atm (e.g. 1.5 to 80 atm), and preferably about 2 to 70 atm. A reaction time can be appropriately selected within a range of, for example, about 30 minutes to 48 hours depending on the reaction temperature and pressure.

The reaction can be performed in a batch system, semi-batch system, continuous system or another conventional system. After the completion of the reaction, reaction products can be easily separated and purified by a conventional technique such as filtration, concentration, distillation, extraction, crystallization, recrystallization, column chromatography, and other separation means, or any combination of these separation means.

If plural compounds can be formed from one organic substrate in the oxidation, one product can be selectively obtained by appropriately choosing the type and amount of the promoter, reaction temperature, reaction time, and other reaction conditions. This holds true for the following reactions.

[Carboxylation]

An organic substrate is allowed to react with carbon monoxide and oxygen in the presence of the nitrogen-containing heterocyclic compound of the formula (1) to introduce a carboxyl group into the organic substrate.

Such organic substrates include, for example, the compounds (b) each having a carbon-hydrogen bond at the adjacent position to an unsaturated bond, the compounds (c) each having a methine carbon atom, the cycloalkanes (d), and the polymers (o). These compounds may have, for example, the aforementioned various substituents.

When the compound (b) having a carbon-hydrogen bond at the adjacent position to an unsaturated bond is allowed to react with carbon monoxide and oxygen in the presence of the catalyst, a carboxyl group is introduced into the carbon atom at the adjacent position to the unsaturated bond. Likewise, when the compound (c) having a methine carbon atom is used as the organic substrate, a carboxyl group is introduced into the methine carbon atom, and when the cycloalkane (d) is used as the organic substrate, a carboxyl group is introduced into a methylene carbon atom constituting a ring. Specifically, for example, 1-adamantanecarboxylic acid is formed from adamantane. When the polymer (o) is allowed to come in contact with carbon monoxide and oxygen, a carboxyl group is introduced into a primary carbon atom (e.g., a methyl carbon atom at the benzyl or allyl position), a secondary carbon atom (e.g., a methylene carbon atom at the benzyl or allyl position; a methylene carbon atom constituting a non-aromatic carbocyclic ring) or a tertiary carbon atom (e.g., a methine carbon atom in a branched alkyl group or alkylene group, a methine carbon atom at a junction position or bridgehead position of a polycyclic group) of the polymer molecule.

The proportion of the carbon monoxide in this reaction is, for example, equal to or more than 1 mole (e.g., about 1 to 100 moles), and preferably about 1.5 to 100 moles, relative to 1 mole of the organic substrate. The proportion of oxygen can be selected within a rang of equal to or more than 0.5 mole (e.g., about 0.5 to 100 moles), and preferably about 0.5 to 30 moles, relative to 1 mole of the organic substrate. The ratio of carbon monoxide to oxygen is such that carbon monoxide/oxygen (by mole) is about 1/99 to 99/1, preferably about 10/90 to 99/1, and more preferably about 50/50 to 95/5.

The carboxylation reaction can be performed in an inert organic solvent. Such organic solvents include the organic solvents exemplified in the description of the oxidation reaction, such as organic acids (e.g., acetic acid), nitriles (e.g., acetonitrile and benzonitrile), and halogenated hydrocarbons (e.g., dichloroethane and trifluoromethylbenzene).

A reaction temperature can be selected depending on, for example, the types of the catalyst and organic substrate and is, for example, about 0° C. to 200° C., preferably about 10° C. to 150° C., and more preferably about 10° C. to 100° C. The reaction can be performed at atmospheric pressure or under a pressure (under a load) in a batch system, semi-batch system, continuous system or another conventional system.

[Nitration]

An organic substrate can be nitrated by allowing the organic substrate to react with the nitrogen oxide in the presence of the catalyst.

Such organic substrate include, but are not limited to, the compounds (b) each having a carbon-hydrogen bond at the adjacent position to an unsaturated bond, the compounds (c) each having a methine carbon atom, the cycloalkanes (d), and the polymers (o). Each of these compounds may have, for example, any of the aforementioned substituents.

In the presence of the catalyst, the reaction of the nitrogen oxide with the compound (b) having a carbon-hydrogen bond at the adjacent position to an unsaturated bond introduces a nitro group into a carbon atom at the adjacent position to the unsaturated bond. The use of the compound (c) having a methine carbon atom as the organic substrate introduces a nitro group into the methine carbon atom, and the use of the (d) cycloalkane introduces a nitro group into a methylene carbon atom constituting a ring. Specifically, for example, 1-nitroethylbenzene is formed from ethylbenzene, and 1-nitroadamantane is formed from adamantane. When the polymer (o) is allowed to come in contact with the nitrogen oxide, a nitro group is introduced into a primary carbon atom (e.g., a methyl carbon atom at the benzyl or allyl position), a secondary carbon atom (e.g., a methylene carbon atom at the benzyl or allyl position; or a methylene carbon atom constituting a non-aromatic carbocyclic ring) or a tertiary carbon atom (e.g., a methane carbon atom in a branched alkyl group or alkylene group; or a methine carbon atom at a junction position or bridgehead position of a polycyclic group) of the polymer molecule.

The amount of the nitrogen oxide can be selected depending on the amount of nitro groups to be introduced and is, for example, equal to or more than 1 mole (e.g., about 1 to 50 moles), and preferably about 1.5 to 30 moles, relative to 1 mole of the organic substrate. In this connection, the amount of the nitrogen oxide may be less than 1 mole relative to 1 mole of the organic substrate. By this configuration, the conversion rate from the nitrogen oxide is markedly improved and the selectivity of a product may be improved in many cases. This process can be therefore employed as a treatment process of nitrogen oxides exhausted from, for example, plants.

The combination use of the nitrogen oxide (especially nitrogen dioxide) with oxygen can improve the reaction rate. In such a combination use, the proportion of the oxygen is, for example, equal to or more than 0.5 mole, preferably about 1 to 100 moles, and more preferably about 2 to 50 moles, relative to 1 mole of the nitrogen oxide.

The nitration reaction can be performed in the presence of, or in the absence of a solvent. Such solvents include, but are not limited to, benzene, and other aromatic hydrocarbons; dichloromethane, chloroform, 1,2-dichloroethane, dichlorobenzene, and other halogenated hydrocarbons; t-butanol, t-amyl alcohol, and other alcohols; acetonitrile, benzonitrile, and other nitriles; acetic acid, propionic acid, and other organic acids; and formamide, acetamide, dimethylformamide (DMF), dimethylacetamide, and other amides. Each of these solvents can be used alone or in combination.

A reaction temperature can be selected depending on, for example, the type of the organic substrate and is, for example, about 0° C. to 150° C., preferably about 25° C. to 125° C., and more preferably about 30° C. to 100° C. The reaction can be performed at atmospheric pressure or under a pressure (under a load), in a batch system, semi-batch system, continuous system or other conventional systems.

When the aforementioned reaction is performed using a chain or cyclic compound having a methylene group as the organic substrate in the co-existence of a halogen or a Beckmann rearrangement catalyst, a corresponding amide is formed from the chain compound, and a corresponding lactam is formed from the cyclic compound. Specifically, ethylbenzene yields, for example, acetanilide, and a cycloalkane yields a lactam having one more members than the cycloalkane (e.g., cyclohexane yields $\epsilon$-caprolactam, cycloheptane yields 7-heptanelactam, and cyclooctane yields 8-octanelactam).

The halogen includes, for example, chlorine, bromine, and iodine. The term "Beckmann rearrangement catalyst" used herein means and includes catalysts or reagents generally used for a Beckmann rearrangement reaction. Typical Beckmann rearrangement catalysts include, but are not limited to, sulfuric acid, hydrochloric acid, hydrobromic acid, hydroiodic acid, polyphosphoric acid, formic acid, boron trifluoride, and other acids (protonic acids and Lewis acids); phosphoryl chloride, phosphorous pentachloride, acetyl chloride, and other halogen-containing compounds; and acetic anhydride, and other acid anhydrides. Such a Beckmann rearrangement catalyst may be formed in the reaction system using a precursor of the catalyst. Each of these halogens and Beckmann rearrangement catalysts can be used alone or in combination. The role of the halogen in the present reaction is supposed to be as follows. The halogen such as chlorine serves as a radical initiator and withdraws a hydrogen from the substrate to be converted into a hydrogen halide, and this hydrogen halide acts as a Beckmann rearrangement catalyst.

The amount of the halogen and Beckmann rearrangement catalyst can be appropriately selected depending on the types thereof in consideration of, for example, the reaction rate and is, for example, about 0.0001 to 1 mole, and preferably about 0.0005 to 0.1 mole, relative to 1 mole of the organic substrate.

The mechanism of this reaction is not sufficiently clarified but is supposed to be as follows. Initially, a methylene group of the substrate is oxidized into a carbonyl group and is then converted into an oxime and is then converted into a corresponding amide or lactam by a Beckmann rearrangement.

[Sulfonation]

When an organic substrate is allowed to react with the sulfur oxide in the presence of the catalyst, the organic substrate can be sulfonated to yield a corresponding sulfonic acid.

Such organic substrates include, but are not limited to, the compounds (b) each having a carbon-hydrogen bond at the adjacent position to an unsaturated bond, the compounds (c) each having a methine carbon atom, the cycloalkanes (d), and the polymers (o). Each of these compounds may have, for example, any of the aforementioned substituents.

In the presence of the catalyst, when the compound (b) having a carbon-hydrogen bond at the adjacent position to an unsaturated bond is allowed to react with the sulfur oxide, a sulfo group (i.e., sulfonic group; $SO_3H$) is introduced into a carbon atom at the adjacent position to the unsaturated bond. The use of the compound (c) having a methine carbon atom as the organic substrate introduces a sulfo group into the methine carbon atom, and the use of the cycloalkane (d) introduces a sulfo group into a methylene carbon atom constituting a ring. Specifically, for example, adamantane yields 1-adamantanesulfonic acid, and cyclohexane yields cyclohexanesulfonic acid. When the polymer (o) is allowed to come in contact with the sulfur oxide, a sulfo group is introduced into a primary carbon atom (e.g., a methyl carbon atom at the benzyl or allyl position), a secondary carbon atom (e.g., a methylene carbon atom at the benzyl or allyl position; or a methylene carbon atom constituting a non-aromatic carbocyclic ring) or a tertiary carbon atom (e.g., a methine carbon atom in a branched alkyl group or alkylene group; or a methine carbon atom at a junction position or bridgehead position of a polycyclic group) of the polymer molecule.

The amount of the sulfur oxide in this reaction can be selected depending on, for example, the amount of sulfo groups to be introduced and is, for example, equal to or more than 1 mole (e.g., about 1 to 50 moles), and preferably about 1.5 to 30 moles, relative to 1 mole of the organic substrate. The combination use of the sulfur oxide (especially, sulfur dioxide) with oxygen can improve the yield of a target compound. The ratio of the sulfur oxide to the oxygen in such a combination use is, for example, such that the former/the latter (by mole) is about 1/99 to 99/1, preferably about 10/90 to 90/10, and more preferably about 30/70 to 70/30.

The sulfonation reaction can be performed in the presence of, or in the absence of a solvent. Such solvents include, for example, the solvents exemplified in the description of the nitration reaction.

A reaction temperature can be selected depending on, for example, the type of the organic substrate and is, for example, about 0° C. to 150° C., preferably about 10° C. to 125° C., and more preferably about 15° C. to 100° C. The reaction can be performed at atmospheric pressure or under a pressure (under a load), in a batch system, semi-batch system, continuous system or other conventional systems.

The produced sulfonic acid can be converted into a corresponding sulfonate by a conventional technique. For example, the sulfonic acid is allowed to react with a compound in an appropriate solvent such as water to yield a corresponding sulfonate. Such compounds include, but are not limited to, alkali metal hydroxides, alkali metal carbonates, alkali metal hydrogencarbonates, alkaline earth metal hydroxides, alkaline earth metal carbonates, amines, and thiourea (isothioureas)

[Other Reactions Using Oxygen as Reactant]

A reaction of (A) a compound capable of forming a stable radical with (B) a radical scavenging compound in the presence of the catalyst and oxygen yields a product of an addition or substitution reaction of the compound (A) and the compound (B) or an oxidized product thereof.

Such compounds (A) capable of forming a stable radical include, for example, (A1) oxygen-atom-containing compounds each having a carbon-hydrogen bond at the adjacent position to an oxygen atom, (A2) carbonyl-group-containing compounds, and (A3) compounds each having a hydrocarbon group with a methine carbon atom. Each of these compounds can be used alone or in combination. These compounds may have various substituents within a range not adversely affecting the reaction.

The oxygen-atom-containing compounds (A1) each having a carbon-hydrogen bond at the adjacent position to an oxygen atom include, for example, (A1-1) primary or secondary alcohols, and (A1-2) ethers each having a carbon-hydrogen bond at the adjacent position to an oxygen atom.

The primary or secondary alcohols (A1-1) include alcohols similar to the aforementioned primary or secondary alcohols (a). Preferred alcohols include secondary alcohols such as 2-propanol, s-butyl alcohol, and other aliphatic secondary alcohols; cyclohexanol, and other alicyclic secondary alcohols, and 1-phenylethanol, and other aromatic secondary alcohols.

The ethers (A1-2) each having a carbon-hydrogen bond at the adjacent position to an oxygen atom include, but are not limited to, dimethyl ether, diethyl ether, dipropyl ether, diisopropyl ether, dibutyl ether, methyl ethyl ether, methyl butyl ether, ethyl butyl ether, diallyl ether, methyl vinyl ether, ethyl allyl ether, and other aliphatic ethers; anisole, phenetole, dibenzyl ether, phenyl benzyl ether, and other aromatic ethers; and tetrahydrofuran, and other cyclic ethers.

The compounds (A2) each containing a carbonyl group include, but are not limited to, acetone, methyl ethyl ketone, 3-pentanone, acetophenone, and other chain ketones; cyclopentanone, cyclohexanone, and other cyclic ketones; biacetyl (2,3-butanedione), 2,3-pentanedione, 3,4-hexanedione, bibenzoyl (benzil), acetylbenzoyl, cyclopentane-1,2-dione, cyclohexane-1,2-dione, and other 1,2-dicarbonylcompounds (e.g., α-diketones); acetoin, benzoin, and other α-keto-alcohols; acetaldehyde, propionaldehyde, butanal, hexanal, and other aliphatic aldehydes; cyclohexyl aldehyde, and other alicyclic aldehydes; benzaldehyde, and other aromatic aldehydes. Preferred carbonyl-group-containing compounds are chain ketones, 1,2-dicarbonyl compounds (e.g., α-diketones), keto-alcohols, and other ketones.

The compounds (A3) each having a hydrocarbon group with a methine carbon atom include (A3-1) cyclic compounds each having a methine group (i.e., a methine carbon-hydrogen bond) as a constitutive unit of a ring, and (A3-2) chain compounds each having a methine carbon atom.

The cyclic compounds (A3-1) include, for example, (A3-1a) bridged cyclic compounds each having at least one methine group, and (A3-1b) non-aromatic cyclic compounds (e.g., alicyclic hydrocarbons) each having a hydrocarbon group bonded to a ring. The bridged cyclic compounds also include compounds in which two rings possess two carbon atoms in common, such as hydrogenated products of condensed polycyclic aromatic hydrocarbons.

The bridged cyclic compounds (A3-1a) include compounds similar to the bridged cyclic compounds (c1-1). The bridged cyclic compounds each have a methine carbon atom at a bridgehead position (corresponding to a junction position when two rings commonly possess two atoms).

The non-aromatic cyclic compounds (A3-1b) each having a hydrocarbon group bonded to a ring include, but are not limited to, 1-methylcyclopentane, 1-methylcyclohexane, limonene, menthene, menthol, carbomenthone, menthone, and other alicyclic hydrocarbons each having about 3 to 15 members and having a hydrocarbon group (e.g., an alkyl group) bonded to its ring, and derivatives thereof. The hydrocarbon group just mentioned above contains about 1 to 20 (preferably 1 to 10) carbon atoms. The non-aromatic cyclic compounds (A3-1b) each having a hydrocarbon group bonded to its ring have a methine carbon atom at the bonding site between the ring and the hydrocarbon group.

The chain compounds (A3-2) each having a methine carbon atom include, but are not limited to, chain hydrocarbons each having a tertiary carbon atom, such as isobutane, isopentane, isohexane, 3-methylpentane, 2,3-dimethylbutane, 2-methylhexane, 3-methylhexane, 3,4-dimethylhexane, 3-methyloctane, and other aliphatic hydrocarbons each having about 4 to 20 (preferably 4 to 10) carbon atoms, and derivatives thereof.

The radical scavenging compounds (B) include (B1) unsaturated compounds, (B2) compounds each having a hydrocarbon group with a methine carbon atom, and (B3) heteroatom-containing compounds. Each of these compounds may be used alone or in combination. These compounds may have various substituents within a range not adversely affecting the reaction. The radical scavenging compound (B) may be a polymer.

The unsaturated compounds (B1) include a wide variety of compounds each having an unsaturated bond. Such compounds include, for example, (B1-1) unsaturated compounds each having an electron attracting group at the adjacent position of a carbon-carbon unsaturated bond [active olefins (electron-deficient olefins) and other active unsaturated compounds], (B1-2) compounds each having a carbon-carbon triple bond, (B1-3) compounds each having an aromatic ring, (B1-4) ketenes, and (B1-5) isocyanate or thioisocyanate compounds.

The active unsaturated compounds (B1-1) include, but are not limited to, methyl (meth)acrylate, ethyl (meth)acrylate, isopropyl (meth)acrylate, phenyl (meth)acrylate, methyl crotonate, ethyl crotonate, methyl 3-methyl-2-butenoate, ethyl 3-methyl-2-butenoate, methyl 2-pentenoate, methyl 2-octenoate, methyl cinnamate, ethyl cinnamate, methyl 4,4,4-trifluoro-2-butenoate, ethyl 4,4,4-trifluoro-2-butenoate, dimethyl maleate, diethyl maleate, dimethyl fumarate, diethyl fumarate, methyl 3-cyanoacrylate, ethyl 3-cyanoacrylate, and other α,β-unsaturated esters; vinyl methyl ketone, vinyl ethyl ketone, methyl 1-propenyl ketone, and other α,β-unsaturated ketones; propenal (acrolein), crotonaldehyde, and other α,β-unsaturated aldehydes; acrylonitrile, methacrylonitrile, and other α,β-unsaturated. nitriles; (meth)acrylic acid, crotonic acid, and other α,β-unsaturated carboxylic acids; (meth)acrylamide, and other α,β-unsaturated carboxylic acid amides; N-(2-propenylidene)methylamine, N-(2-butenylidene)methylamine, and other α,β-unsaturated imines; styrene, vinyltoluene, α-methylstyrene, β-methylstyrene, and other styrene derivatives, and other compounds each having an aryl group bonded at the adjacent position to a carbon-carbon unsaturated bond; butadiene, isoprene, 2-chlorobutadiene, 2-ethylbutadiene, vinylacetylene, cyclopentadiene derivatives, and other conjugated dienes (including compounds in which a double bond and a triple bond are conjugated).

The compounds (B1-2) each having a carbon-carbon triple bond include, for example, methylacetylene and 1-butyne. The compounds (B1-3) each having an aromatic ring include, for example, compounds each having a benzene ring, a naphthalene ring, or another aromatic carbocyclic ring; and compounds each having a pyrrole ring, a furan ring, a thiophene ring, or another aromatic heterocyclic ring. The ketenes (B1-4) include, for example, ketene, and 2-methylketene. The isocyanate or thioisocyanate compounds (B1-5) include, for example, methyl isocyanate, ethyl isocyanate, phenyl isocyanate, methyl thioisocyanate, ethyl thioisocyanate, and phenyl thioisocyanate.

The compounds (B2) each having a hydrocarbon group with a methine carbon atom include the compounds exemplified as the compounds (A3). In the reaction, the same compound can be employed as the compound (A3) and the compound (B2).

The heteroatom-containing compounds (B3) include, for example, (B3-1) compounds each having a sulfur atom, (B3-2) compounds each having a nitrogen atom, (B3-3) compounds each having a phosphorus atom, and (B3-4) compounds each having an oxygen atom. The compounds (B3-1) each having a sulfur atom include, for example, sulfides and thiols. The compounds (B3-2) each having a nitrogen atom include, for example, amines. The compounds (B3-3) each having a phosphorus atom include, for example, phosphites. The compounds (B3-4) each having an oxygen atom include, for example, N-oxides.

This reaction yields a product of addition or substitution reaction corresponding to a combination of the compound (A) capable of forming a stable radical and the radical scavenging compound (B).

For example, when the oxygen-atom-containing compound (A1) having a carbon-hydrogen bond at the adjacent position to an oxygen atom is employed as the compound (A), the adjacent position to the oxygen atom is bonded to an atom (e.g., a carbon atom) constituting an unsaturated bond of the unsaturated compound (B1), to the methine carbon atom of the compound (B2) having a hydrocarbon group with a methine carbon atom, or to the heteroatom of the heteroatom-containing compound (B3). Thus, an addition or substitution reaction product is obtained.

When the carbonyl-group-containing compound (A2) is employed as the compound (A), a bond between a carbonyl group and an atom adjacent to the carbonyl group is broken, and an atomic group containing the carbonyl group (e.g., an acyl group) is bonded to the aforementioned position of the compound (B1), (B2) or (B3) to yield an addition or substitution reaction product. When the compound (A3) containing a hydrocarbon group with a methine carbon atom is employed as the compound (A) capable of forming a stable radical, the methine carbon atom is bonded to the aforementioned position of the compound (B1), (B2) or (B3) to yield an addition or substitution reaction product.

Generally, the use of the unsaturated compound (B1) as the radical scavenging compound (B) yields an addition reaction product, and the use of the compound (B2) having a hydrocarbon group with a methine carbon atom as the compound (B) yields a substitution reaction product (e.g., a coupling product).

According to this process, an oxidized product of the addition or substitution reaction product can be formed. For example, when the reaction is performed in the presence of oxygen using the unsaturated compound (B1) as the radical scavenging compound (B), a group derived from the compound (A) is bonded to one carbon atom of the two carbon atoms constituting the unsaturated bond as mentioned above, and a hydroxyl group can be introduced to the other carbon atom.

A reaction mechanism is not clarified in detail, but is supposed as follows. The oxygen acts upon the nitrogen-containing heterocyclic compound of the formula (1) and a radical is formed on an oxygen atom bonded to a nitrogen atom of the nitrogen-containing heterocyclic compound, and this radical withdraws a hydrogen from the compound (A), and of the compound (A), a radical is then generated on a carbon atom at the adjacent position to an oxygen atom in the compound (A1), on a carbonyl carbon atom in the compound (A2), or on a methine carbon atom in the compound (A3). This radical attacks an atom constituting an unsaturated bond, the methine carbon atom, or the heteroatom of the compound (B). Subsequently, the above oxidation proceeds under some conditions.

This process can yield a variety of organic compounds by allowing an appropriate combination of the compound (A) capable of forming a table radical and the radical scavenging compound (B) to react with each other.

For example, when a 1,2-dicarbonyl compound or its hydroxy reductant [as the compound (A)] is allowed to react with the radical scavenging compound (B) in the presence of the catalyst and oxygen, an acyl group is introduced into the radical scavenging compound (B).

Such 1,2-dicarbonyl compounds include the 1,2-dicarbonyl compounds (e.g., α-diketones) exemplified as the carbonyl-group-containing compounds (A2). Hydroxy reductants of the 1,2-dicarbonyl compounds include the α-keto-alcohols exemplified as the carbonyl-group-containing compounds (A2) and the vicinal diols exemplified as the primary or secondary alcohols (A1-1).

As the radical scavenging compounds (B), the compounds (B2) each having a hydrocarbon group with a methine carbon atom are particularly preferred. When the compound (B2) is used, an acyl group is introduced into the methine carbon atom.

The amount of the 1,2-dicarbonyl compound or its hydroxy reductant in the reaction in question is, for example, equal to or more than 1 mole (e.g., about 1 to 50 moles), preferably about 1.5 to 20 moles, and more preferably about 3 to 10 moles, relative to 1 mole of the radical scavenging compound (B). The 1,2-dicarbonyl compound or its hydroxy reductant can be also used as a reaction solvent. The amount of the oxygen is generally equal to or more than 0.5 mole (e.g., equal to or more than 1 mole), preferably about 1 to 100 moles, and more preferably about 2 to 50 moles, relative to 1 mole of the radical scavenging compound (B).

The proportion of the nitrogen-containing compound of the formula (1) is, for example, about 0.00001 to 1 mole, preferably about 0.001 to 0.7 mole, and more preferably about 0.01 o 0.5 mole, relative to 1 mole of the radical scavenging compound (B). The use of the metallic compound as a promoter in this reaction can markedly improve the yield of a target compound. The proportion of the metallic compound is, for example, about 0.00001 to 1 mole, preferably about 0.0001 to 0.1 mole, and more preferably about 0.001 to 0.05 mole, relative to 1 mole of the radical scavenging compound (B).

The reaction is generally performed in an organic solvent, Such organic solvents include, for example, the solvents exemplified in the description of the oxidation. A reaction temperature can be appropriately selected depending on, for example, the type of the radical scavenging compound (B) and is, for example, about 0° C. to 300° C., preferably about 30° C. to 250° C., and more preferably about 40° C. to 200° C. The reaction is generally performed at a temperature of about 40° C. to 150° C. in many cases. The reaction can be conducted at atmospheric pressure or under a pressure (under a load) in a batch system, semi-batch system, continuous system, or any other conventional systems.

According to the above process, an acyl group (e.g., acetyl group upon the use of biacetyl or its hydroxy reductant) corresponding to the 1,2-dicarbonyl compound can be introduced into even a carbon atom which is not activated with, for example, a carbonyl group. An acyl-group-containing compound can be therefore obtained in a good yield. This is probably because the reaction undergoes a radical mechanism. Particularly, an acyl-group-containing compound having an acyl group introduced into a methine carbon atom can be obtained in a high yield from a compound having a methine carbon atom. For example, the acylation of a bridged cyclic hydrocarbon such as adamantane yields an acyl-group-containing compound having an acyl group at a bridgehead position. Likewise, the acylation of a chain compound having a methine carbon atom such as isobutane yields a t-alkyl ketone such as t-butyl ketone.

Such reactions of the compound (A) capable of forming a stable radical with the radical scavenging compound (B) also include the following reaction. Specifically, (A11) an alcohol of the following formula (4):

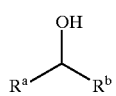

(4)

wherein each of $R^a$ and $R^b$ is, identical to or different from each other, a hydrogen atom or an organic group, where $R^a$ and $R^b$ maybe combined to form a ring with the adjacent carbon atom, is allowed to react with (B11) an active olefin of the following formula (5):

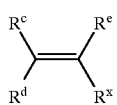

(5)

wherein each of $R^c$, $R^d$, and $R^e$ is, identical to or different from one another, a hydrogen atom or an organic group; and $R^x$ is an electron attracting group, where $R^c$ and $R^d$ may be combined to form a ring with the adjacent carbon atom, and $R^c$ and $R^e$ or $R^d$ and $R^x$ may be respectively combined to form a ring with the adjacent carbon-carbon bond, in the presence of the catalyst and oxygen to yield a 1,3-dihydroxy compound of the following formula (6):

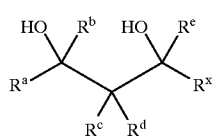

(6)

wherein $R^a$, $R^b$, $R^c$, $R^d$, $R^e$, and $R^x$ have the same meanings as defied above.

Organic groups in $R^a$ and $R^b$ include, for example, hydrocarbon groups and heterocyclic groups. Such hydrocarbon groups include, but are not limited to, methyl, ethyl, propyl, isopropyl, butyl, isobutyl, s-butyl, t-butyl, pentyl, hexyl, octyl, decyl, tetradecyl, hexadecyl, octadecyl, allyl, and other straight- or branched-chain aliphatic hydrocarbon groups (alkyl groups, alkenyl groups and alkynyl groups) each having about 1 to 20, preferably about 1 to 10, and more preferably about 1 to 6 carbon atoms; cyclopentyl, cyclohexyl, and other alicyclic hydrocarbon groups each having about 3 to 15 carbon atoms; and phenyl, naphthyl, and other aromatic hydrocarbon groups each having about 6 to 14 carbon atoms. These hydrocarbon groups may have a variety of substituents. Such substituents include, but are not limited to, halogen atoms, oxo group, hydroxyl group, substituted oxy groups (e.g., alkoxy groups, aryloxy groups, and acyloxy groups), carboxyl groups, substituted oxycarbonyl groups, substituted or unsubstituted carbamoyl groups, cyano group, nitro group, substituted or unsubstituted amino groups, alkyl groups (e.g., methyl, ethyl, and other $C_1$–$C_4$ alkyl groups), cycloalkyl group, aryl groups (e.g., phenyl and naphthyl groups), and heterocyclic groups.

Heterocyclic rings constituting the heterocyclic groups in $R^a$ and $R^b$ include aromatic heterocyclic rings and non-aromatic heterocyclic rings. Such heterocyclic rings include, but are not limited to, heterocyclic rings each containing an oxygen atom as a heteroatom (e.g., furan, tetrahydrofuran, oxazole, isoxazole, and other 5-membered rings, 4-oxo-4H-pyran, tetrahydropyran, morpholine, and other 6-membered rings, benzofuran, isobenzofuran, 4-oxo-4H-chromene, chroman, isochroman, and other condensed rings), heterocyclic rings each containing a sulfur atom as a heteroatom (e.g., thiophene, thiazole, isothiazole, thiadiazole, and other 5-membered rings, 4-oxo-4H-thiopyran, and other 6-membered rings, benzothiophene and other condensed rings), heterocyclic rings each containing a nitrogen atom as a heteroatom (e.g., pyrrole, pyrrolidine, pyrazole, imidazole, triazole, and other 5-membered rings, pyridine, pyridazine, pyrimidine, pyrazine, piperidine, piperazine, and other 6-membered rings, indole, indoline, quinoline, acridine, naphthyridine, quinazoline, purine, and other condensed rings).

The rings formed by $R^a$ and $R^b$ with the adjacent carbon atom include, but are not limited to, cyclobutane, cyclopentane, cyclohexane, cyclohexene, cyclooctane, cyclododecane, and other non-aromatic carbocyclic rings each having about 3 to 20 members. These rings may have substituents, and another ring (a non-aromatic ring or an aromatic ring) may be condensed to these rings.

The organic groups in $R^c$, $R^d$, and $R^e$ can be any organic groups that are not reactive under reaction conditions. Such organic groups include, but are not limited to, halogen atoms, hydrocarbon groups, heterocyclic groups; substituted oxycarbonyl groups (e. g ., alkoxycarbonyl groups, aryloxycarbonyl groups, aralkyloxycarbonyl groups, and cycloalkyloxycarbonyl groups), carboxyl group, substituted or unsubstituted carbamoyl groups (N-substituted or unsubstituted amide groups), cyano group, nitro group, sulfur acid radicals (sulfonic acid groups, and sulfinic acid groups), sulfur acid ester groups (sulfonic ester groups, and sulfinic ester groups), acyl groups, hydroxyl group, alkoxy groups, and N-substituted or unsubstituted amino groups. The carboxyl group, hydroxyl group, and amino groups may be protected by a conventional protective group.

The halogen atoms include fluorine, chlorine, bromine, and iodine atoms. The hydrocarbon groups include, for example, the groups exemplified as the hydrocarbon groups in $R^a$ and $R^b$. These hydrocarbon groups may have any of the aforementioned substituents. Preferred hydrocarbon groups include, for example, methyl, ethyl, propyl, isopropyl, butyl, isobutyl, s-butyl, t-butyl, vinyl, allyl, and other straight- or branched-chain aliphatic hydrocarbon groups (alkyl groups, alkenyl group, and alkynyl groups) each having about 1 to 6 carbon atoms (particularly about 1 to 4 carbon atoms); phenyl group, naphthyl group, and other aromatic hydrocarbon groups each having about 6 to 14 carbon atoms; cycloalkyl groups; trifluoromethyl group, and other haloalkyl groups each having about 1 to 6 carbon atoms (particularly about 1 to 4 carbon atoms).

The heterocyclic groups include, for example, the groups exemplified as the heterocyclic groups in $R^a$ and $P^b$. These heterocyclic groups may have any of the substituents. The alkoxycarbonyl groups include, but are not limited to, methoxycarbonyl, ethoxycarbonyl, propoxycarbonyl, isopropoxycarbonyl, butoxycarbonyl, t-butoxycarbonyl, and other $C_1$–$C_6$ alkoxy-carbonyl groups. The aryloxycarbonyl groups include, but are not limited to, phenyloxycarbonyl group, and the aralkyloxycarbonyl groups include, for example, benzyloxycarbonyl group. Illustrative cycloalkyloxycarbonyl groups are cyclopentyloxycarbonyl, and cyclohexyloxycarbonyl groups.

The substituted carbamoyl groups include, for example, N-methylcarbamoyl, and N,N-dimethylcarbamoyl groups. Illustrative sulfonic acid ester groups are methyl sulfonate, ethyl sulfonate, and other sulfonic acid $C_1$–$C_4$ alkyl ester groups. Illustrative sulfinic acid ester groups are methyl sulfinate, ethyl sulfinate, and other sulfinic acid $C_1$–$C_4$ alkyl ester groups. The acyl groups include, but are not limited to, acetyl, propionyl, and other aliphatic acyl groups (e.g., $C_2$–$C_7$ aliphatic acyl groups), and benzoyl, and other aromatic acyl groups. The alkoxy groups include, but are not limited to, methoxy, ethoxy, propoxy, butoxy, and other alkoxy groups each having about 1 to 6 carbon atoms. The N-substituted amino groups include, for example, N,N-dimethylamino, N,N-diethylamino, and piperidino groups.

The rings formed by $R^c$ and $R^d$ with the adjacent carbon atom include, but are not limited to, cyclopropane, cyclobutane, cyclopentane, cyclopentene, cyclohexane, cyclohexene, cyclooctane, cyclododecane, and other non-aromatic carbocyclic rings (cycloalkane rings and cycloalkene rings) each having about 3 to 20 members. These rings may have substituents, and another ring (a non-aromatic ring or aromatic ring) may be condensed to these rings.

The rings formed by $R^c$ and $R^e$ with the adjacent carbon-carbon bond include, but are not limited to, cyclopropene, cyclobutene, cyclopentene, cyclohexene, cyclooctene, cyclododecene, and other cycloalkene rings each having about 3 to 20 members. These rings may have substituents, and another ring (a non-aromatic ring or aromatic ring) may be condensed to these rings.

Illustrative electron attracting groups $R^x$ include, but are not limited to, methoxycarbonyl, ethoxycarbonyl, and other alkoxycarbonyl groups; phenoxycarbonyl, and other aryloxycarbonyl groups; formyl, acetyl, propionyl, benzoyl, and other acyl groups; cyano group; carboxyl group; carbamoyl, N,N-dimethylcarbamoyl, and other substituted or unsubstituted carbamoyl groups; —CH=N—R, where R is, for example, an alkyl group; phenyl, naphthyl, and other aryl groups; vinyl, 1-propenyl, ethynyl, and other 1-alkenyl groups or 1-alkynyl groups.

The rings which may be formed by $R^d$ and $R^x$ with the adjacent carbon-carbon bond include, for example, cyclopentadiene ring, pyrrole ring, furan ring, and thiophene ring.

Typical examples of the alcohols of the formula (4) include the compounds exemplified as the primary or secondary alcohols (a), and typical examples of the active olefins of the formula (5) include the compounds exemplified as the active unsaturated compounds (B1-1).

When $R^x$ in the compound of the formula (6) formed by the reaction is an alkoxycarbonyl group, aryloxycarbonyl group or another ester group or a carboxyl group, a cyclization reaction may further proceed in the system to yield a furanone derivative (γ-butyrolactone derivative) of the following formula (7):

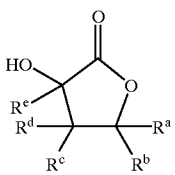

(7)

wherein $R^a$, $R^b$, $R^c$, $R^d$, and $R^e$ have the same meanings as defined above. The yield of the furanone derivative can be improved by controlling the type and proportion of the co-catalyst or further subjecting the product to aging after the addition reaction (or further oxidation reaction). A reaction temperature in the aging period is set higher than that in the addition reaction in many cases. The furanone derivative can be also produced by isolating the compound of the formula (6), for example dissolving the compound in a solvent, and heating the solution according to necessity.

When $R^x$ in the compound of the formula (5) is an acyl group such as formyl group, acetyl group, propionyl group, or benzoyl group, a β-acyloxycarboxylic acid or β-acyloxyketone of the following formula (8):

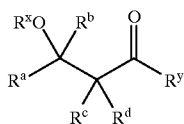

(8)

wherein $R^y$ is a hydroxyl group when $R^e$ in the formula (5) is a hydrogen atom, and $R^y$ is the substituent $R^e$ when $R^y$ is another group than a hydrogen atom; and $R^a$, $R^b$, $R^c$, $R^d$, and $R^x$ have the same meanings as defined above, is further formed. This is provably because the rearrangement of the $R^x$ group (acyl group) and oxidation of a carbon atom to which the acyl group has been bonded proceed in a system after the formation of the compound of the formula (6)

This reaction is generally performed in an organic solvent. Such organic solvents include, for example, the solvents exemplified in the description of the oxidation.

The ratio of the alcohol of the formula (4) to the active olefin of the formula (5) can be appropriately selected depending on the types (costs, reactivity) of the both compounds and combination thereof. For example, the alcohol of the formula (4) can be used in excess amounts (e.g., about 2 to 50 times by mole) relative to the active olefin of the formula (5), or vice versa, the active olefin of the formula (5) can be used in excess amounts to the alcohol of-the formula (4).

A reaction temperature can be appropriately selected depending on, for example, the types of the alcohol of the formula (4) and the active olefin of the formula (5) and is, about 0° C. to 300° C., preferably about 20° C. to 200° C., more preferably about 30° C. to 150° C., and often about 40° C. to 100° C. The reaction can be performed at atmospheric pressure or under a pressure (under a load) in a batch system, semi-batch system, continuous system or another conventional system.

As thus described, the invention can introduce an oxygen-atom-containing group such as a hydroxyl group, oxo group, ether group (—O—), carboxyl group, nitro group, or sulfo group into an organic substrate under mild conditions. The invented process does not particularly require exhaust gas treatments. In addition, an appropriate combination of organic substrates can form a carbon-carbon bond under mild conditions. Furthermore, the invention can be applied to a wide variety of reactions using oxygen-atom-containing reactants and is therefore highly versatile.

The present invention will now be illustrated in further detail with reference to several examples below, which are not intended to limit the scope of the invention.

EXAMPLE 1

A mixture of 2 mmol of 9H-xanthene, 0.2 mmol of 6-trifluoromethyl-l-hydroxybenzotriazole, 0.01 mmol of acetylacetonatomanganese(II), and 6 ml of acetic acid was stirred at 80° C. in an oxygen atmosphere (1 atm) for 6 hours. A gas chromatographic analysis of products in a reaction mixture found that 9H-xanthene was converted into xanthone in a yield of 52% with a conversion rate of 70%.

EXAMPLE 2

A mixture of 3 mmol of fluorene, 0.3 mmol of 3,4-dihydro-3-hydroxy-4-oxo-1,2,3-benzotriazine, 0.015 mmol of acetylacetonatocobalt(II), and 5 ml of acetic acid was stirred at 100° C. in an oxygen atmosphere (1 atm) for 2 hours. A gas chromatographic analysis of products in a reaction mixture found that fluorenone was formed in a yield of 30%.

EXAMPLE 3

A mixture of 10 mmol of adamantane, 0.8 mmol of 6-trifluoromethyl-1-hydroxybenzotriazole, 0.06 mmol of acetylacetonatocobalt(III), and 25 ml of acetic acid was stirred at 90° C. in an oxygen atmosphere (1 atm) for 8 hours. A gas chromatographic analysis of products in a reaction mixture found that 1-adamantanol and 1,3-adamantanediol were formed in yields of 38% and 4%, respectively, with a conversion rate from adamantane of 48%.

EXAMPLE 4

A mixture of 3 mmol of 1-octene, 15 mmol of benzhydrol, 0.3 mmol of 6-trifluoromethyl-1-hydroxybenzotriazole, 0.6 mmol of hexafluoroacetone trihydrate, and 3 ml of trifluoromethylbenzene was stirred at 90° C. in an oxygen atmosphere (1 atm) for 24 hours. A gas chromatographic analysis of products in a reaction mixture found that 1,2-epoxyoctane was formed in a yield of 34% with a conversion rate from 1-octene of 40%.

EXAMPLE 5

A mixture of 2 mmol of cyclohexanone, 20 mmol of cyclohexanol, 0.4 mmol of 6-trifluoromethyl-1-hydroxybenzotriazole, 0.6 mmol of hexafluoroacetone trihydrate, and 1 ml of benzonitrile was stirred at 80° C. in an oxygen atmosphere (1 atm) for 12 hours. A gas chromatographic analysis of products in a reaction mixture found that ε-caprolactone was formed in a yield of 27% (on the basis of cyclohexanone).

EXAMPLE 6

In a reactor, 10 mmol of adamantane, 1 mmol of 6-trifluoromethyl-1-hydroxybenzotriazole, 0.005 mmol of acetylacetonatocobalt(II), and 25ml of acetic acid were placed, and a gas back containing carbon monoxide and oxygen sealed therein (1 liter of carbon monoxide, 0.5 liter of oxygen; pressure: 5 kgf/cm$^2$) was mounted to the reactor.

The charge was then stirred at 60° C. for 6 hours. A gas chromatographic analysis of products in a reaction mixture found that 1-adamantanecarboxylic acid was formed in a yield of 26% with a conversion rate from adamantane of 34%.

EXAMPLE 7

A side-arm egg plant type flask was immersed in ice water and the inside of the flask was reduced in pressure. Nitrogen monoxide was introduced from a gas pack into the flask, and the same volume of oxygen was introduced from another gas pack into the flask. The inside of the flask was filled with a reddish brown gas, and a blue liquid mainly containing $N_2O_3$ was formed while the reddish brown gas was settling out. The introduction procedures of nitrogen monoxide and oxygen were repeated, and the formed blue liquid was frozen with liquid nitrogen.

Separately, 1 mmol of adamantane, 0.05 mmol of 6-trifluoromethyl-1-hydroxybenzotriazole, and 5 ml of acetic acid were placed and were mixed in a flask. The above-prepared frozen blue liquid (0.024 mole in terms of $N_2O_3$) was placed in the flask. The resulting mixture was stirred and reacted at 100° C. for 10 hours. A gas chromatographic analysis of products in a reaction mixture found that 1-nitroadamantane was formed in a yield of 18% with a conversion rate from adamantane of 21%.

EXAMPLE 8

A mixture of 2 mmol of adamantane, 0.2 mmol of 6-trifluoromethyl-1-hydroxybenzotriazole, 0.01 mmol of vanadyl acetylacetonato [VO(acac)$_2$], and 5ml of acetic acid was stirred at 40° C. in a sulfur dioxide ($SO_2$) (0.5 atm) and oxygen (0.5 atm) atmosphere for 2 hours. A gas chromatographic analysis of products in a reaction mixture found that the conversion rate from adamantane was 40%. The reaction mixture was extracted with water, was neutralized with a sodium hydroxide aqueous solution, and was made weakly acidic with hydrochloric acid. Excess amounts of a benzyl-isothiourea hydrochloride aqueous solution was then added to the mixture to precipitate benzylthiuronium salt of 1-adamantanesulfonic acid in a yield of 29%.

EXAMPLE 9

A mixture of 3 mmol of adamantane, 9 mmol of biacetyl, 0.3 mmol of 6-trifluoromethyl-1-hydroxybenzotriazole, 0.0006 mmol of cobalt(II) acetate, and 3 ml of acetic acid was stirred at 60° C. in an oxygen atmosphere (1 atm) for 4 hours. A gas chromatographic analysis of products in a reaction mixture found that 1-acetyladamantane was formed in a yield of 26% with a conversion rate from adamantane of 32%.

EXAMPLE 10

A mixture of 3 mmol of ethyl acrylate, 3 ml of 2-propanol, 0.6 mmol of 6-trifluoromethyl-l-hydroxybenzotriazole, 0.003 mmol of cobalt(II) acetate, 0.015 mmol of acetylacetonatocobalt(III), and 1 ml of acetonitrile was stirred at 60° C. in an oxygen atmosphere (1 atm) for 12 hours. A gas chromatographic analysis of products in a reaction mixture found that ethyl 2,4-dihydroxy-4-methylpentanoate and (α-hydroxy-γ,γ-dimethyl-γ-butyrolactone were formed in yields of 2% and 28%, respectively, with a conversion rate from ethyl acrylate of 62%.

[Spectrum Data of α-Hydroxy-γ,γ-dimethyl-γ-butyrolactone]

$^1$H-NMR (CDCl$_3$) δ: 1.42 (s, 3H), 1.51 (s, 3H), 2.06 (dd, 1H), 2.52 (dd, 1H), 3.03 (brs, 1H), 4.63 (t, 1H)

Other embodiments and variations will be obvious to those skilled in the art, and this invention is not to be limited to the specific matters stated above.

What is claimed is:

1. A catalyst for a reaction using an oxygen-atom-containing reactant, said catalyst comprising a nitrogen-containing heterocyclic compound shown by the following formula (1):

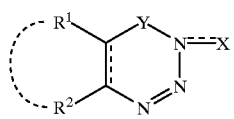

(1)

wherein each of $R^1$ and $R^2$ is, identical to or different from each other, a hydrogen atom, a halogen atom, an alkyl group, a haloalkyl group, an aryl group, a cycloalkyl group, a hydroxyl group, an alkoxy group, a carboxyl group, an alkoxycarbonyl group, or an acyl group, and $R^1$ and $R^2$ may be combined to form a double bond or to form an aromatic or non-aromatic ring with the adjacent two carbon atoms, where one or two of heterocyclic ring containing three nitrogen atoms indicated in the formula may be further formed on said $R^1$ or $R^2$ or on said double bond or aromatic or non-aromatic ring formed together by $R^1$ and $R^2$; X is an oxygen atom or a hydroxyl group; and Y is a single bond, a methylene group, or a carbonyl group.

2. A catalyst according to claim 1, wherein said oxygen-atom-containing reactant is at least one compound selected from oxygen, carbon monoxide, nitrogen oxides, and sulfur oxides.

3. A catalyst according to claim 1, wherein said nitrogen-containing compound shown by the formula (1) is a compound shown by the following formula (1a) or (1b):

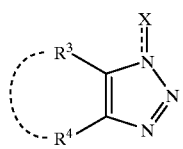

(1a)

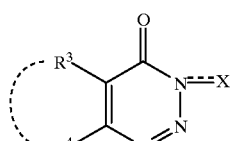

(1b)

wherein each of $R^3$ and $R^4$ is, identical to or different from each other, a hydrogen atom, a halogen atom, an alkyl group, a haloalkyl group, an aryl group, a cycloalkyl group, a hydroxyl group, an alkoxy group, a carboxyl group, an alkoxycarbonyl group, or an acyl group, and $R^3$ and $R^4$ may be combined to form an aromatic 6-membered ring with the adjacent two carbon atoms, where one or two of N-substituted triazole ring or N-substituted triazinone ring indicated in the formulae may be formed on $R^3$ or $R^4$ or on said aromatic 6-membered ring; and X is an oxygen atom or a hydroxyl group.

4. A catalyst according to claim 1, comprising a combination of said nitrogen-containing heterocyclic compound shown by the formula (1) with at least one compound selected from the group consisting of (i) metallic compounds, (ii) organic salts each composed of a polyatomic cation or a polyatomic anion and its counter ion, said polyatomic cation or anion containing a Group 15 or Group 16 element of the Periodic Table of Elements, and said element being combined with at least one organic group, (iii) strong acids, and (iv) compounds each having a carbonyl group combined with an electron attracting group.

5. A process for producing an organic compound, said process comprising the step of allowing an organic substrate to react with an oxygen-atom-containing reactant in the presence of a catalyst for a reaction using an oxygen-atom-containing reactant, said catalyst comprising a nitrogen-containing heterocyclic compound shown by the following formula (1):

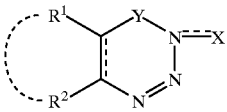

(1)

wherein each of $R^1$ and $R^2$ is, identical to or different from each other, a hydrogen atom, a halogen atom, an alkyl group, a haloalkyl group, an aryl group, a cycloalkyl group, a hydroxyl group, an alkoxy group, a carboxyl group, an alkoxycarbonyl group, or an acyl group, and $R^1$ and $R^2$ may be combined to form a double bond or to form an aromatic or non-aromatic ring with the adjacent two carbon atoms, where one or two of heterocyclic ring containing three nitrogen atoms indicated in the formula may be further formed on said $R^1$ or $R^2$ or on said double bond or aromatic or non-aromatic ring formed together by $R^1$ and $R^2$; X is an oxygen atom or a hydroxyl group; and Y is a single bond, a methylene group, or a carbonyl group, to yield a product having an introduced group containing at least an oxygen atom.

* * * * *